(12) United States Patent
Delaney et al.

(10) Patent No.: US 10,966,648 B2
(45) Date of Patent: Apr. 6, 2021

(54) IDENTIFYING STRESS LEVELS ASSOCIATED WITH CONTEXT SWITCHES

(71) Applicant: INTERNATIONAL BUSINESS MACHINES CORPORATION, Armonk, NY (US)

(72) Inventors: John V. Delaney, Meath (IR); Sean T. Fomash, Hudson, NH (US); Anthony M. Hunt, Hopewell Junction, NY (US); Maeve O'Reilly, Wicklow (IR); Clea A. Zolotow, Key West, FL (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 118 days.

(21) Appl. No.: 16/283,884

(22) Filed: Feb. 25, 2019

(65) Prior Publication Data

US 2019/0183399 A1    Jun. 20, 2019

Related U.S. Application Data

(62) Division of application No. 14/878,528, filed on Oct. 8, 2015, now Pat. No. 10,258,272.

(51) Int. Cl.
*A61B 5/16* (2006.01)
*H04L 29/08* (2006.01)
*A61B 5/00* (2006.01)
*A61B 5/024* (2006.01)

(52) U.S. Cl.
CPC .......... *A61B 5/165* (2013.01); *A61B 5/02405* (2013.01); *A61B 5/4519* (2013.01);
(Continued)

(58) Field of Classification Search
CPC ... A61B 5/165; A61B 5/02405; A61B 5/4519; A61B 5/486; A61B 5/7278; A61B 2503/24; H04L 67/22
See application file for complete search history.

(56) References Cited

U.S. PATENT DOCUMENTS 6,599,243 B2    7/2003  Woltermann et al.
10,258,272 B2*  4/2019  Delaney ............... A61B 5/4519
(Continued)

FOREIGN PATENT DOCUMENTS

EP    2729912    5/2014
FR    2987917    9/2013
(Continued)

OTHER PUBLICATIONS

"How Long Does It Take to Refocus After Context Switching?" http://cogsci.stackexchange.com/questions/4993/how-long-does-it-take-to-refocus-after-context-switching 3 pages. Accessed Oct. 7, 2015.

(Continued)

*Primary Examiner* — Catherine M Voorhees
*Assistant Examiner* — Roland Dinga
(74) *Attorney, Agent, or Firm* — Brian Restauro; Andrew M. Calderon; Roberts Calderon Safran & Cole, P.C.

(57) ABSTRACT

A computer-implemented method includes: receiving, by a computing device, information identifying a user's activity; determining, by the computing device, the user's tasks based on the information identifying the user's activity; determining, by the computing device, the user's context switches based on the user's tasks; receiving, by the computing device, biometrics data associated with the user via an application programming interface (API); determining, by the computing device, the user's stress levels at various times based on the biometrics data; storing, by the computing device, information linking the user's stress level with the user's context switches; and outputting, by the computing device, the information linking the user's stress level with the user's context switches.

17 Claims, 7 Drawing Sheets

(52) U.S. Cl.
CPC ............ *A61B 5/486* (2013.01); *A61B 5/7278* (2013.01); *H04L 67/22* (2013.01); *A61B 2503/24* (2013.01)

(56) References Cited

U.S. PATENT DOCUMENTS

| | | | |
|---|---|---|---|
| 2005/0288954 | A1 | 12/2005 | McCarthy et al. |
| 2011/0225515 | A1 | 9/2011 | Goldman et al. |
| 2013/0018957 | A1 | 1/2013 | Pamaby et al. |
| 2013/0280682 | A1 | 10/2013 | Levine et al. |
| 2014/0287387 | A1 | 9/2014 | Vukasinovic et al. |
| 2015/0297140 | A1* | 10/2015 | Hernandez ............ A61B 5/165 600/547 |
| 2015/0305675 | A1 | 10/2015 | Miller et al. |
| 2017/0100066 | A1 | 4/2017 | Delaney et al. |

FOREIGN PATENT DOCUMENTS

| | | |
|---|---|---|
| WO | 2011055628 | 12/2011 |
| WO | 2013004706 | 1/2013 |

OTHER PUBLICATIONS

"Multitasking: Switching costs", http://www.apa.org/research/action/multitask.aspx., American Psychological Association, Mar. 20, 2006, 2 pages.

"Stress Symptoms, Signs, & Causes: The Effects of Stress Overload and What You Can Do About It", http://www.helpguide.org/articles/stress/stress-symptoms-causes-and-effects.htm, 5 pages. Accessed Oct. 7, 2015.

Myers, Steve, "ENTJs and Stress", Team Technology, http://www.teamtechnology.co.uk/personality/types/entj/stress/ 1 page. Accessed Oct. 7, 2015.

Myers, Steve, "Myers Briggs Types and Stress", Team Technology, http://www.teamtechnology.co.uk/myersbriggs/types/entj/stress/ 1 page. Accessed Oct. 7, 2015.

Mark, Gloria, "The Cost of Interrupted Work: More Speed and Stress", CHI 2008 Proceedings, Apr. 5-10, 2008, pp. 107-110.

"List of IBM Patents or Patent Applications Treated as Related",1 page.

* cited by examiner

700

| Person A | |
|---|---|
| From | To |
| Technical Task #1 | Technical Task #2 |
| Technical Task #1 | Coffee Break |
| Technical Task #1 | Resolving customer issue |
| Resolving customer issue | Attending status meeting |
| Resolving customer issue | Snack break |

| Person A | | |
|---|---|---|
| From | To | Stress Score |
| Technical Task #1 | Technical Task #2 | 1 |
| Technical Task #1 | Coffee Break | -2 |
| Technical Task #1 | Resolving customer issue | 4 |
| Resolving customer issue | Attending status meeting | 2 |
| Resolving customer issue | Snack break | -3 |
| | | |
| Average Stress Score | | 0.4 |

IDENTIFYING STRESS LEVELS ASSOCIATED WITH CONTEXT SWITCHES

BACKGROUND

The present invention generally relates to monitoring stress levels in individuals, and more particularly, to determining the stress impact on an individual when switching tasks or multitasking.

Individuals and workers often multitask during the normal course of a day. For example, workers often work on several different projects in a day, and switch from different types of tasks (e.g., reading/writing e-mails, attending meetings, assisting customers, etc.). The frequency at which an individual switches tasks, and the types of tasks in which the individual transitions can substantially impact an individual's stress level.

Stress levels may also impact a person's behavior. For example, as an individual's stress increases, a person may behave more to type (e.g., an introvert may become more introverted, and extrovert may become more extroverted). Under extreme stress, an individual's "shadow" may appear (e.g., an introvert will become extroverted, and vice versa).

SUMMARY

In an aspect of the invention, a computer-implemented method includes: receiving, by a computing device, information identifying a user's activity; determining, by the computing device, the user's tasks based on the information identifying the user's activity; determining, by the computing device, the user's context switches based on the user's tasks; receiving, by the computing device, biometrics data associated with the user via an application programming interface (API); determining, by the computing device, the user's stress levels at various times based on the biometrics data; storing, by the computing device, information linking the user's stress levels with the user's context switches; and outputting, by the computing device, the information linking the user's stress levels with the user's context switches.

In another aspect of the invention, there is a computer program product for analyzing stress associated with context switches. The computer program product includes a computer readable storage medium having program instructions embodied therewith. The program instructions are executable by a computing device to cause the computing device to: monitor a user's tasks based on the information identifying the user's activity; monitor the user's context switches based on the user's tasks; tag the user's context switches with respective timestamps indicating when the context switches occurred; receive biometrics data associated with the user via an application programming interface (API); determine the user's stress levels at various times based on the biometrics data; store information linking the user's stress level with the user's context switches; and output the information linking the user's stress level with the user's context switches.

In another aspect of the invention, a system includes a CPU, a computer readable memory and a computer readable storage medium associated with a computing device; program instructions to monitor a user's communication feeds; program instructions to parse the user's communication feeds; program instructions to determine the user's tasks based on parsing the user's communication feeds; program instructions to determine the user's context switches based on determining the user's tasks; program instructions to receive biometrics data associated with the user via an application programming interface (API); program instructions to determine the user's stress levels at various times based on the biometrics data; program instructions to store information linking the user's stress level with the user's context switches; and program instructions to output the information linking the user's stress level with the user's context switches. The program instructions are stored on the computer readable storage medium for execution by the CPU via the computer readable memory

BRIEF DESCRIPTION OF THE DRAWINGS

The present invention is described in the detailed description which follows, in reference to the noted plurality of drawings by way of non-limiting examples of exemplary embodiments of the present invention.

FIG. 7A and FIG. 7B show example context switching stress tables in accordance with aspects of the present invention.

DETAILED DESCRIPTION

Figure 1:
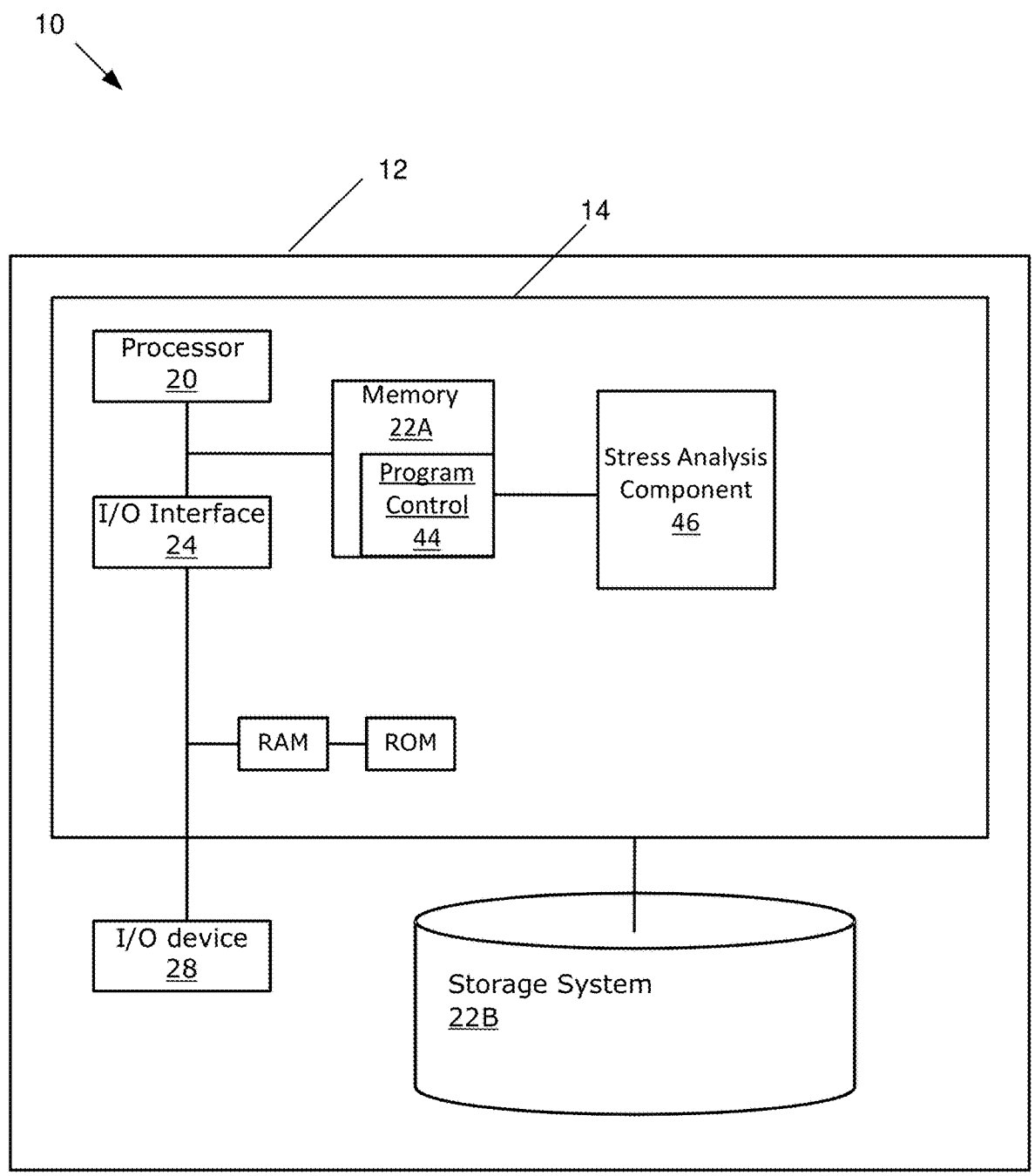
FIG. 1 shows an illustrative environment for managing the processes in accordance with the invention.

The present invention generally relates to monitoring stress levels in individuals, and more particularly, to determining the stress impact on an individual when switching tasks or multitasking. In accordance with aspects of the present invention, information identifying the number and types of task switches (e.g., transitioning from performing one task to performing another task) is used to determine a stress indicator or score for a user. This stress indicator may assist the user to identify how his or her stress level is impacted when transitioning from one type of task to another, and to better plan tasks throughout the day in order to optimize or reduce stress levels. Also, management personnel may use the stress indicators from a group of users or employees to proactively reduce or manage the stress of their employees by re-arranging tasks. A reduction in stress levels, advantageously, may lead to a more productive workforce.

In embodiments, information identifying the breadth of tasks a user is performing may be used to count the number of context switches (e.g., transitions from one task to another). Further, stress scores or indicators may be assigned to each context switch based on the user's physical reactions that indicate the individual's stress level. For example, wearable biometrics devices may be used to determine the user's stress level, and a link can be established between the user's stress level and the context switch. Also, the type of context switch is determined based on user activity information. For example, the type of context switch identifies that the user transitioned from one task to another (e.g., from working on one project to working on another project, or working on one project followed by performing some other task, such as attending a meeting, taking a coffee break, etc.).

In embodiments, user activity information is used to determine when a context switch occurs, and the type of context switch. For example, user activity information, such as the user's social media postings, instant messages, e-mail messages, calendar events, phone records, document editing activity, user location, and/or other information identifying the user's activity may be used to identify when the user has transitioned from performing one task to performing a different task. The user's stress level during the transition may be measured using biometrics devices, and information linking the user's stress level during the transition can be provided to the user and/or to other interested personnel (e.g., workplace managers, family members, etc.). In embodiments, a report may be generated identifying a list of context switches or transitions experienced by the user over a period of time (e.g., a day, a week, etc.). Further, the report may identify the types of context switch, or the activities to and from which the user transitioned. The report may identify the stress level at each context switch, and may further identify an aggregate stress level for the user during the period of time. Based on information in the report, a user can identify ways to reduce his or her overall stress level. As an illustrative example, if the report identifies that a user's stress level is lower when transitioning from Task A to Task B than it is when transitioning from Task A to Task C, the user can modify his or her future schedule to replace transitions from Task A to Task C with transitions from Task A to Task B.

In embodiments, a report may be generated based on stress level information relating to context switches for a group for multiple users having certain commonalities (e.g., users with similar job titles, length of service, users working for the same department or manager, users having similar personality types, etc.). Thus, the report may identify average stress levels for users by category (job titles, department, personality types, etc.). Also, identifying an individual's stress level based on personality type may provide insight into the individuals' behavior under different levels of stress.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the flowchart illustrations, and combinations of blocks in the flowchart illustrations, can be implemented by special purpose hardware-based systems that perform the specified functions or acts or carry out combinations of special purpose hardware and computer instructions.

FIG. 1 shows an illustrative environment 10 for managing the processes in accordance with the invention. To this extent, environment 10 includes a server 12 or other computing system that can perform the processes described herein. In particular, server 12 includes a computing device 14. The computing device 14 can be resident on a network infrastructure or computing device of a third party service provider (any of which is generally represented in FIG. 1).

The computing device 14 also includes a processor 20 (e.g., CPU), memory 22A, an I/O interface 24, and a bus 26. The memory 22A can include local memory employed during actual execution of program code, bulk storage, and cache memories which provide temporary storage of at least some program code in order to reduce the number of times code must be retrieved from bulk storage during execution. In addition, the computing device includes random access memory (RAM), a read-only memory (ROM), and an operating system (O/S).

The computing device 14 is in communication with external I/O device/resource 28 and storage system 22B. For example, I/O device 28 can comprise any device that enables an individual to interact with computing device 14 (e.g., user interface) or any device that enables computing device 14 to communicate with one or more other computing devices using any type of communications link. The external I/O device/resource 28 may be for example, a handheld device, PDA, handset, keyboard etc.

In general, processor 20 executes computer program code (e.g., program control 44), which can be stored in memory 22A and/or storage system 22B. Moreover, in accordance with aspects of the invention, program control 44 controls a stress analysis component 46, e.g., the processes described herein. The stress analysis component 46 can be implemented as one or more program code in program control 44 stored in memory 22A as separate or combined modules. Additionally, the stress analysis component 46 may be implemented as separate dedicated processors or a single or several processors to provide the function of these tools. While executing the computer program code, the processor 20 can read and/or write data to/from memory 22A, storage system 22B, and/or I/O interface 24. The program code executes the processes of the invention. The bus 26 provides a communications link between each of the components in computing device 14.

The computing device 14 can comprise any general purpose computing article of manufacture capable of executing computer program code installed thereon (e.g., a personal computer, server, etc.). However, it is understood that computing device 14 is only representative of various possible equivalent-computing devices that may perform the processes described herein. To this extent, in embodiments, the functionality provided by computing device 14 can be implemented by a computing article of manufacture that includes any combination of general and/or specific purpose hardware and/or computer program code. In each embodiment, the program code and hardware can be created using standard programming and engineering techniques, respectively.

Similarly, server 12 is only illustrative of various types of computer infrastructures for implementing the invention. For example, in embodiments, server 12 comprises two or more computing devices (e.g., a server cluster) that communicate over any type of communications link, such as a network, a shared memory, or the like, to perform the process described herein. Further, while performing the processes described herein, one or more computing devices on server 12 can communicate with one or more other computing devices external to server 12 using any type of communications link. The communications link can comprise any combination of wired and/or wireless links; any combination of one or more types of networks (e.g., the Internet, a wide area network, a local area network, a virtual private network, etc.); and/or utilize any combination of transmission techniques and protocols.

Figure 2:
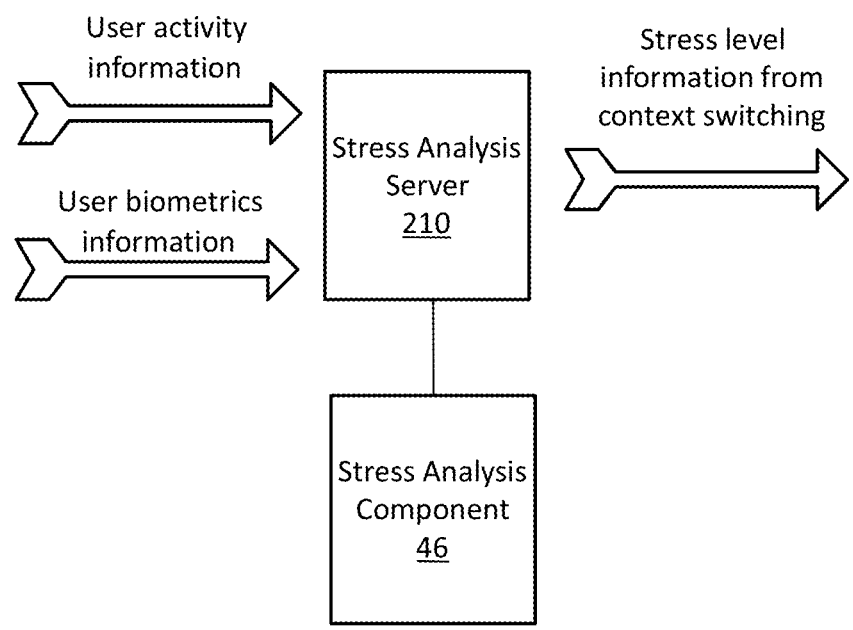
FIG. 2 shows an overview of an example implementation in accordance with aspects of the present invention.

FIG. 2 shows an overview of an example implementation in accordance with aspects of the present invention. As shown in FIG. 2, user activity information and biometrics information for a particular user are received by a stress analysis server 210 (e.g., a server or computing device that implements the stress analysis component 46). As described above, the stress analysis server 210 may determine context switches based on the user activity. For example, the stress analysis server 210 may determine a time in which a user transitioned from one task to another based on the user activity. Further, the stress analysis server 210 may obtain biometrics information to determine the user's stress level at the time the user transitioned from one activity to another. The stress analysis server 210 may output information identifying the user's stress level from context switching (e.g., in the form of a report). For example, the stress analysis server 210 may display the report, publish the report, or output the report to a computing device of the user and/or an interested party.

Figure 3:
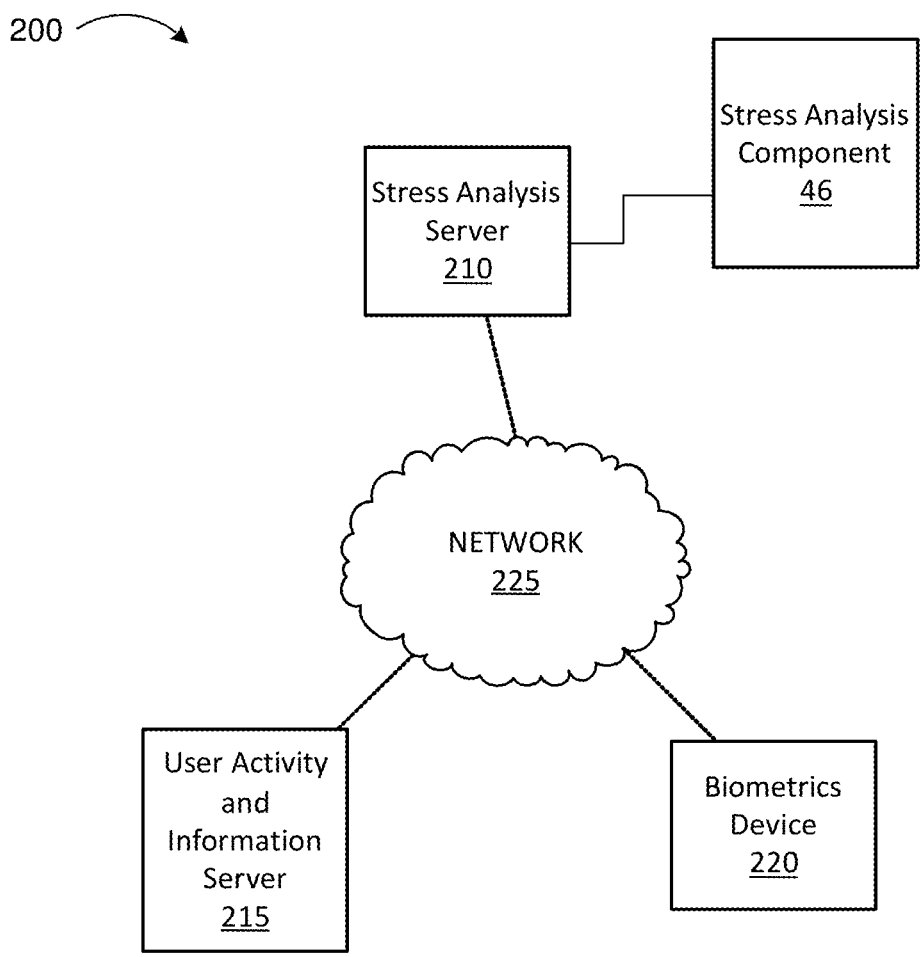
FIG. 3 shows an example environment in accordance with aspects of the present invention.

FIG. 3 shows an example environment in accordance with aspects of the present invention. As shown in FIG. 3, environment 200 may include stress analysis server 210, user activity and information server 215, biometrics device 220, and/or network 225.

The stress analysis server 210 may include one or more computing devices that implement the stress analysis component 46. The stress analysis server 210 may receive user activity and/or user information from the user activity and information server 215, and biometrics information for the user from the biometrics device 220. Based on the user activity information, the stress analysis server 210 may identify when the user experiences a context switch (e.g., transitions from one task to another), and the user's stress level associated with the context switch (e.g., based on the biometrics information received from the biometrics device 220). As described in greater detail below, the stress analysis server 210 may parse through the communication feeds identifying the user's activity to identify the tasks that a user is performing.

The user activity and information server 215 may include one or more computing devices that stores user activity information regarding a user. For example, the user activity and information server 215 may store information identifying a task that the user is currently performing (e.g., a work-related technical task, resolving a customer issue, attending a meeting, taking a meal break, etc.). In embodiments, the user activity and information server 215 may store a user's instant messages (e.g., from the user's social network account, personal/work instant messaging accounts, etc.), network usage activity (e.g., indicating networks or websites being accessed by the user), social media activity (e.g., public postings on the user's social media account), interactive media feeds (e.g., blog posts made by the user), e-mail messages, calendar events, telephone calling activity, location information, etc.) In embodiments, the user activity and information server 215 may store other information regarding the user, such as the user's job title, personality profile, etc. This information may be used to group stress level indicators from many users having certain commonalities (e.g., users with similar job titles, users working for the same department or manager, users having similar personality types, etc.).

The biometrics device 220 may include one or more wearable devices that track a user's biometrics and physical reactions, such as heart rate variability (HRV), pulse, muscle tension, and/or other biometrics data. For example, the biometrics device may include a watch, necklace, eyeglasses, clothing, etc. with biometrics sensors (e.g., heart rate sensors, muscle tension sensors, etc.). The biometrics device 220 may provide the biometrics data to the stress analysis server 210 so that the stress analysis server 210 can determine a stress level indicator for the user when then user transitions from one task to another.

The network 225 may include one or more wired and/or wireless networks. For example, the network 225 may include a cellular network (e.g., a second generation (2G) network, a third generation (3G) network, a fourth generation (4G) network, a fifth generation (5G) network, a long-term evolution (LTE) network, a global system for mobile (GSM) network, a code division multiple access (CDMA) network, an evolution-data optimized (EVDO) network, or the like), a public land mobile network (PLMN), and/or another network. Additionally, or alternatively, the network 225 may include a local area network (LAN), a wide area network (WAN), a metropolitan network (MAN), the Public Switched Telephone Network (PSTN), an ad hoc network, a managed Internet Protocol (IP) network, a virtual private network (VPN), an intranet, the Internet, a fiber optic-based network, and/or a combination of these or other types of networks.

The quantity of devices and/or networks in the environment 200 is not limited to what is shown in FIG. 3. In practice, the environment 200 may include additional devices and/or networks; fewer devices and/or networks; different devices and/or networks; or differently arranged devices and/or networks than illustrated in FIG. 3. Also, in some implementations, one or more of the devices of the environment 200 may perform one or more functions described as being performed by another one or more of the devices of the environment 200. Devices of the environment 200 may interconnect via wired connections, wireless connections, or a combination of wired and wireless connections.

Figure 4:
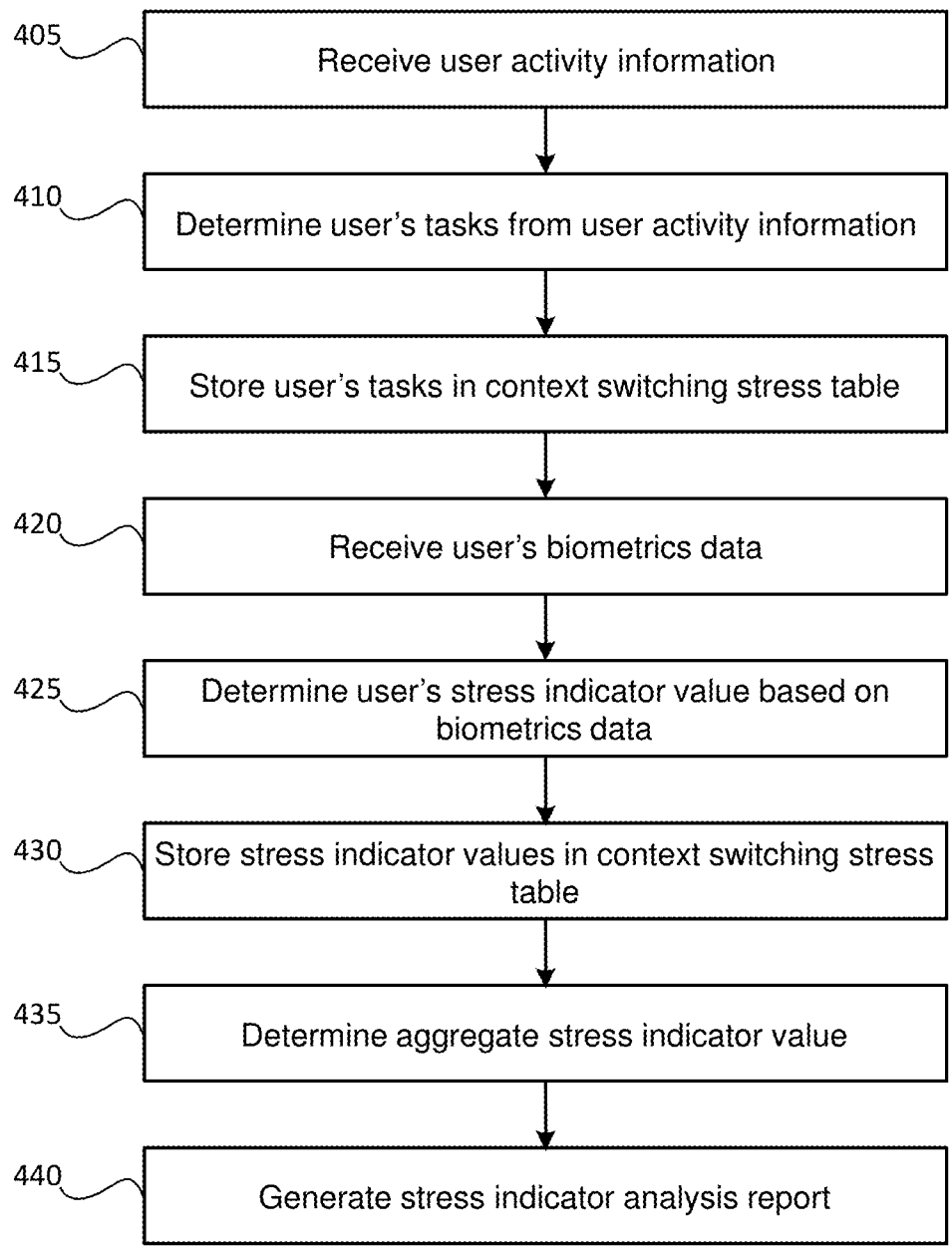
FIG. 4 shows an example flowchart for generating a stress indicator analysis report in accordance with aspects of the present invention.

FIG. 4 shows an example flowchart for generating a stress indicator analysis report in accordance with aspects of the present invention. The steps of FIG. 4 may be implemented in the environment of FIG. 3, for example, and are described using reference numbers of elements depicted in FIG. 3. As noted above, the flowchart illustrates the architecture, functionality, and operation of possible implementations of systems, methods, and computer program products according to various embodiments of the present invention.

At step 405, user activity information is received. For example, the stress analysis server 210 may receive user activity information for a particular user from the user activity and information server 215. In embodiments, the user activity information may include communications feeds associated with the users, such as the user's social media postings, instant messages, e-mail messages, calendar events, etc. Further, the user activity information may include phone records/usage activity, document editing activity, network usage activity, user location, and/or other information identifying the user's activity. In embodiments, the user may manually update a diary, timecard, or record identifying the user's activity, although in a preferred embodiment, the user's activity is identified with minimal to no manual entries of activity by the user. Additional details regarding the receipt of user activity information by the stress analysis server 210 is described in greater detail below with respect to FIG. 5.

At step 410, the user's tasks are determined from the user activity information. For example, the user's communications feeds may be parsed to identify tasks that the user has been performing. In embodiments, verbs and subjects may be extracted from the communication feeds to identify possible tasks the user is performing. For example, communications feeds may be parsed to identify that the user is assisting a customer based on an instant message or instant message status, such as "Assisting customers—please do not disturb." The stress analysis server 210 may identify the user's tasks based on a database that links particular verbs and subjects with particular tasks. Additional details regarding parsing the user's communication feed to identify the user's tasks are described in greater detail below with respect to FIG. 6.

In embodiments, the user's tasks may further be identified based on phone records/usage activity, document editing activity, network usage activity, user location, and/or other information identifying the user's activity. For example, the phone records may identify whether the user is on a work-related or personal call based on a telephone number of the individual or party that the user is speaking with. Further, the telephone number may identify the user's task (e.g., if the user is on a company teleconference, assisting a customer, etc.).

The user's document editing activity may identify the title and/or type of document that the user is working on based on an extension of the document, (e.g., a word processing document, a presentation document, a database document, etc.). The title and/or type of document may indicate the user's task based on a subject in the title (e.g., a presentation type document with the title "Client meeting presentation" may indicate that the user is working on a work-related presentation).

The user's network usage activity may identify files and/or directories that the user is accessing, (e.g., within a network, such as a company network). For example, different directories and files may be associated with different tasks and the user's accessing of different directories and files may indicate the user's tasks. Also, the user's location may indicate the user's task (e.g., different locations in an office building may indicate the user's tasks). For example, if the user is located in a meeting room, a determination may be made that the user is attending a meeting. As another example, if the user is located in a cafeteria, a determination may be made that the user is taking a meal break. In embodiments, the stress analysis server 210 may identify the user's tasks based on a customizable database that links telephone numbers, document types, subjects in document titles, network usage activity, user location, and/or other information with the user's tasks.

In embodiments, the stress analysis server 210 may tag the user's tasks and the user's context switches with timestamps. As described in greater detail below, the user's tasks and context switches may be linked with stress indicator values based on timestamps of the context switches and timestamps associated with the stress indicator values.

At step 415, the user's tasks are stored in a context switching stress table. For example, based on identifying the user's tasks at step 410, the stress analysis server 210 may store the tasks in a context switching stress table. In embodiments, the stress analysis server 210 may monitor the user's activity to monitor the user's tasks. The stress analysis server 210 may store information identifying a transition from one task to another in the context switching stress table. As further described in FIG. 7A, each entry in the context switching stress table may identify a task from which the user transitioned to a subsequent task.

At step 420, the user's biometrics data are received. For example, the stress analysis server 210 may receive the user's biometrics data (e.g., heart rate variation data, pulse data, body temperature, etc.) from one or more biometrics devices 220. The stress analysis server 210 may monitor the biometrics data in order to determine the user's stress level when performing individual tasks, and further, to determine the user's stress level when transitioning from one task to another. In embodiments, the stress analysis server 210 stores timestamps associated with the biometrics data.

At step 425, the user's stress indicator value (e.g., stress level) is determined based on the biometrics data. For example, the stress analysis server 210 may determine the user's stress level using any number of conventional techniques that determines stress levels using biometrics data. In some embodiments, the stress analysis server 210 may determine the user's stress level using heart rate variability (HRV) measurements and patterns. For example, HRV may be used to determine stress levels since HRV indicates stress-inducing and relaxation-related changed. Also, muscle tension measurements may also be used to determine stress levels.

In a preferred embodiment, the user's stress level may be determined when the user transitions from one task to another. Additionally, the user's stress level may be determined while the user is performing a particular task. In embodiments, the stress analysis server 210 may determine the user's stress level on a scale (e.g., a scale of 1-5 with a value of 1 being a minimal stress reaction when transitioning from one task to another, and a value of 5 being a severe stress reaction when transitioning from one task to another). Additionally, or alternatively, the user's stress level may be on a scale of −1 to −5 with a value of −1 being a minor de-stressing reaction when transitioning from one task to another, and −5 being a major de-stress reaction when transitioning from one task to another. In embodiments, the user's stress level may be on a binary scale (e.g., 0 or 1) in which 0 denotes a de-stressing reaction and 1 denoting a stressing reaction. In embodiments, the stress analysis server 210 may store timestamps associated with the stress indicator values so that the stress indicator values are linked to tasks and context switches based on timestamps of the tasks and context switches.

At step 430, the stress indicator values are stored in the context switching stress table. For example, the stress analysis server 210 may store the stress indicator values are stored in the context switching stress table. The stress analysis server 210 may store information linking the stress indicator values with the tasks or context switches based on the timestamps of the stress indicator values and the context switches. As described in greater detail below with respect to FIG. 7B, the context switching stress table may store multiple entries, each of which identifies a task from which the user transitioned to a subsequent task, and the user's stress indicator value during the transition.

In embodiments, the context switching stress table may be populated over time to identify the user's stress levels for different context switches. In embodiments, information in the context switching stress table may be used to later predict the user's stress levels based on their context switches even when biometrics data is not available (e.g., since the context switching stress table was originally populated when biometrics data was available).

At step 435, an aggregate stress indicator value is determined. For example, the stress analysis server 210 may determine an aggregate stress indicator value for the user based on multiple stress indicator values associated with multiple context switches. In embodiments, the stress analysis server 210 may receive a request from to determine an aggregate stress indicator for the user over the course of a particular time period (e.g., a particular day, week, month, etc.). The aggregate stress indicator value may factor in the individual stress indicator values from the context switches over the course of the particular time.

At step 440, a stress indicator analysis report is generated. For example, the stress analysis server 210 may generate the stress indicator analysis report based on the information stored in the context switching stress table. For example, the report may indicate the stress indicator values for each context switch for the user. In embodiments, the report may identify the aggregate stress indicator value for the user over a period of time.

In embodiments, the stress analysis server 210 may store context switching stress tables for multiple different users. Accordingly, the stress analysis server 210 may generate a report identifying the stress indicator values for multiple different users. In embodiments, the stress analysis server 210 may generate a report that identifies the stress indicator values of users meeting certain criteria or having particular commonalities (e.g., users of similar personality types, job titles, or users who work in the same department, have the same manager, etc.). In embodiments, data in the report may be sorted in ascending or descending order of stress indicator values (e.g., to identify individuals having the highest stress indicator values, and/or context switches that have the highest stress values). Based on context switches that have the highest stress values, adjustments can be made to a user's schedule to minimize those context switches that have the highest stress values. Also, adjustments may be made to the schedules of those individuals who have commonalities and whose stress indicator values are relatively higher. For example, the schedule of individuals of a particular job title may be adjusted based on information indicating that these individuals experience higher levels of stress than others.

Figure 5:
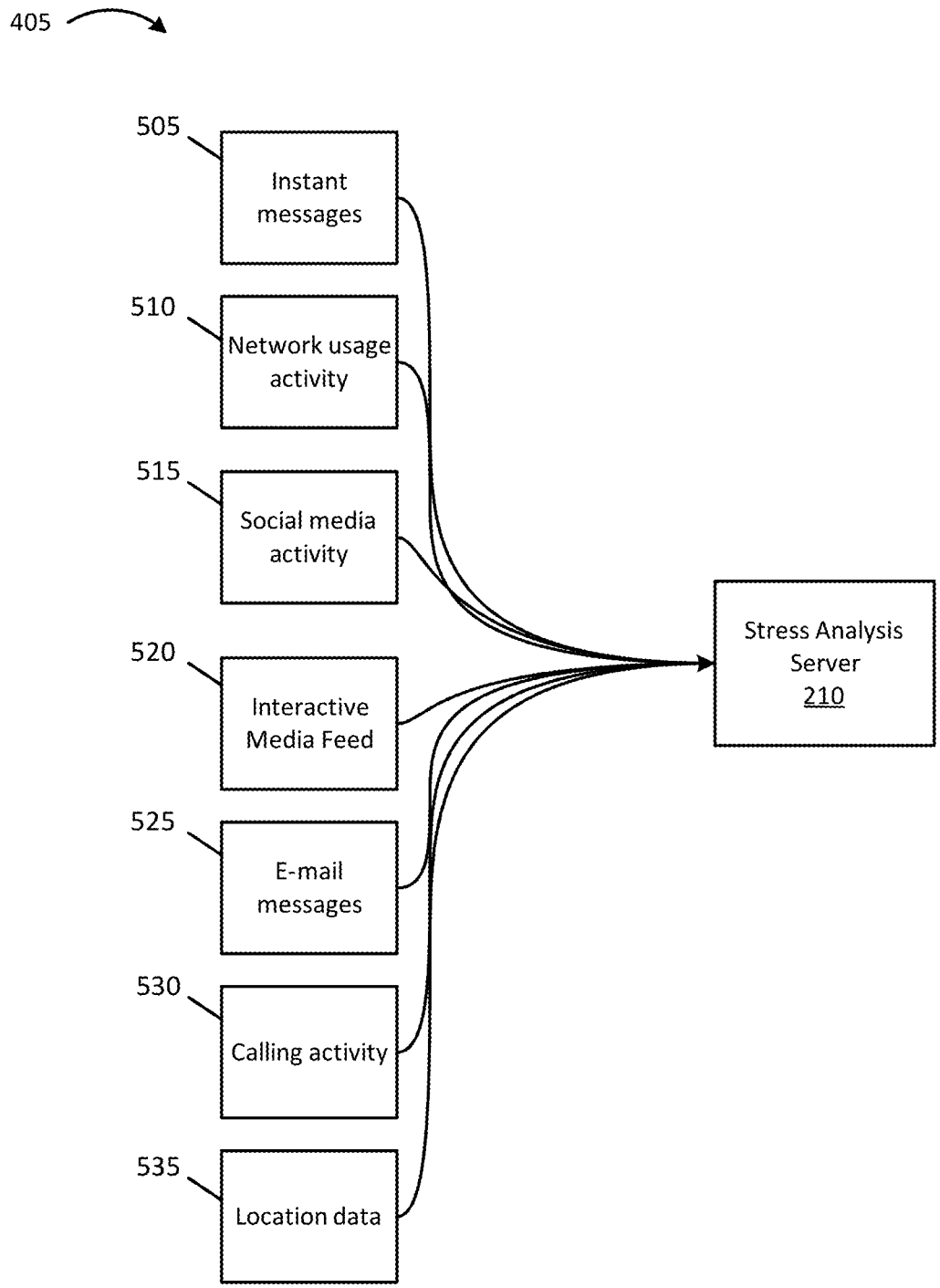
FIG. 5 shows an example of user activity information that may be received by a stress analysis server in accordance with aspects of the present invention.

FIG. 5 shows an example of user activity information that may be received by the stress analysis server 210. The user activity information may be received in accordance with step 405 as previously shown in FIG. 4. As shown in FIG. 5, examples of user activity information that the stress analysis server 210 may receive include:

Instant messages 505. In embodiments, the instant messages may be from the user's social media, e-mail, and/or other instant messaging account. Further, the instant messages may include status updates posted via instant messaging applications. The text in instant messages may be parsed to identify the user's tasks.

Network activity usage 510. In embodiments, the stress analysis server 210 may monitor the user's network activity to identify files and/or directories the user is accessing. Additionally, or alternatively, the stress analysis server 210 may monitor websites accessed by the user. The network activity usage may indicate the tasks that the user is performing. For example, the stress analysis server 210 may store a database that links network activity usage to tasks.

Social media activity 515. In embodiments, the social media activity may include shared postings, messages, check-ins, event responses, etc. The text in the user's postings and messages may be parsed to identify the user's tasks.

Interactive media feed 520. In embodiments, the interactive media feed may include blog postings and/or other postings made by the user. The text in the user's postings and may be parsed to identify the user's tasks.

E-mail messages 525. In embodiments, text in the user's e-mail and may be parsed to identify the user's tasks. Also, calendar events associated with the user's e-mail account may be used to identify the user's tasks at different points in time.

Calling activity 530. In embodiments, the user's calling activity may be analyzed to identify parties with whom the user was conversing. The parties with whom the user was conversing may be determined based on telephone numbers in the user's call records, and may identify the user's tasks (e.g., personal call, work-related call, customer call, etc.).

Location data 535. In embodiments, the user's location data may be received from the user's mobile phone and/or other location tracking device. The location data may be used only when user has consented to share his or her location data. The location data may potentially be used to identify the user's task based on their location. For example, if the user is in a meeting room, a determination may be made that the user is attending a meeting, whereas if the user is in a cafeteria, a determination may be made that the user is taking a meal break.

Figure 6:
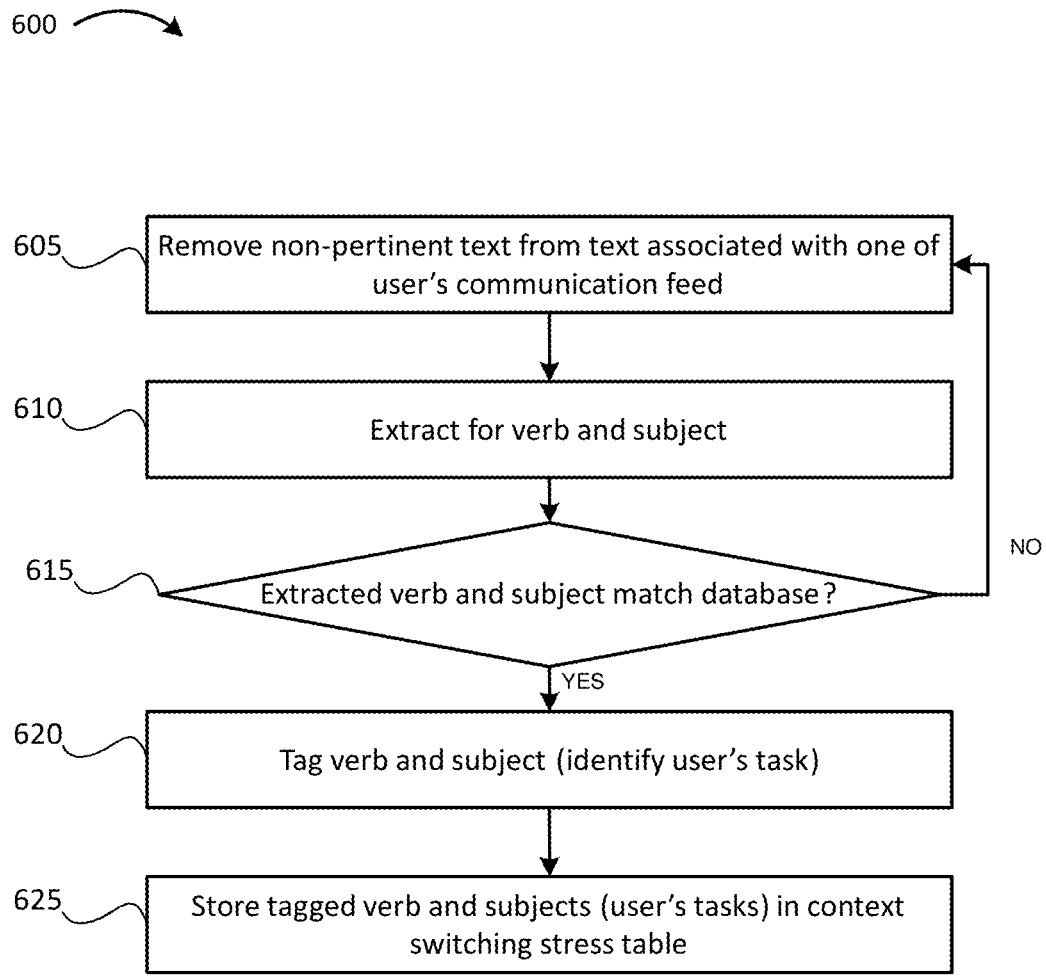
FIG. 6 shows an example flowchart for determining a user's tasks based on the user's communication feeds in accordance with aspects of the present invention.

FIG. 6 shows an example flowchart for determining a user's tasks based on the user's communication feeds in accordance with aspects of the present invention. The steps of FIG. 6 may be implemented in the environment of FIG. 3, for example, and are described using reference numbers of elements depicted in FIG. 3. As noted above, the flowchart illustrates the architecture, functionality, and operation of possible implementations of systems, methods, and computer program products according to various embodiments of the present invention.

The process of FIG. 6 may correspond to process steps within step 410 of FIG. 4 as described above. More specifically, the process of FIG. 6 may be used to identify a user's task based on the user's communication feeds (e.g., instant messages, e-mail messages, social media activity, etc.). Process 600 may be repeated for each of the user's communication feeds (e.g., each of the user's instant messages, e-mail messages, social media postings, etc.).

At step 605, non-pertinent text from text associated with one of the user's communication feeds are removed. For example, verbs such as "working" and "presenting" often appear immediately before subjects, such as "customer issue" or "status meeting." Accordingly, text in the user's communication feed that do not follow or precede (e.g., within a threshold number of words) a verb may be removed (e.g., by the stress analysis server 210).

At step 610, a verb and subject are extracted. For example, the stress analysis server 210 may extract verbs and subjects from the user's communication feed. At step 615, a determination is made as to whether the extracted verb and subject match a database that stores pertinent verbs and subjects corresponding to the user's tasks. If the extracted verb and subject do not match (step 615—NO), this text is removed (step 605), and verbs and subjects are again extracted for a subsequent portion of communications feed (step 610).

If the extracted verb and subject match the database (step 615—YES), at step 620, the verb and subject are tagged (e.g., identified as the user's task). For example, the stress analysis server 210 may tag the verb and subject. In embodiments, step 615 may be omitted, and the originally extracted verb and subjects may be tagged and identified as the user's task.

At step 625, the tagged verb and subject (e.g., the user's task) is stored in the context switching stress table. For example, the stress analysis server 210 may store the identified user's task in the context switching stress table as described above with respect to step 415 in FIG. 4.

FIG. 7A and FIG. 7B show example context switching stress tables in accordance with aspects of the present invention. As shown in FIG. 7A, each entry in a context switching stress table 700 for a particular user (e.g., "Person A") identifies a task from which the user transitioned to a subsequent task. As an illustrative example, the context switching stress table 700 identifies that the user transitioned from "Technical task #1" to "Technical task #2." This information may be derived from the user activity information as described in steps 405, 410, and 415 as described above with respect to FIG. 4. Additional example context switches are further shown in FIG. 7A. In embodiments, the context switching stress table 700 may include timestamps indicating times at which the user switched contexts or transitioned from one task to another.

Referring to FIG. 7B, context switching stress table 750 for the particular user may be populated with stress indicator values (e.g., stress scores) when stress analysis server 210 receives biometrics data. The stress analysis server 210 may populate the context switching stress table 750 with the stress indicator values based on the timestamps of the stress indicator values and the timestamps of the context switches. In embodiments, the context switching stress table 750 may identify the user's average stress score (e.g., the aggregate stress indicator value) based on the individual stress scores for each context switch. In embodiments, the average stress score may be based on individual stress scores for different time periods (e.g., an average stress score for a particular day, week, month, etc.).

As described above, stress levels for a user may be determined at each context switch. Further, an aggregate stress level may further be identified for the user during the period of time. Based on this information, a user can identify ways to reduce his or her overall stress level, and employers can better manage their employees tasks to reduce overall company stress and improve productivity.

In embodiments, a service provider, such as a Solution Integrator, could offer to perform the processes described herein. In this case, the service provider can create, maintain, deploy, support, etc., the computer infrastructure that performs the process steps of the invention for one or more customers. These customers may be, for example, any business that uses technology. In return, the service provider can receive payment from the customer(s) under a subscription and/or fee agreement and/or the service provider can receive payment from the sale of advertising content to one or more third parties.

In still additional embodiments, the invention provides a computer-implemented method for determining stress levels of users based on context switches, via a network. In this case, a computer infrastructure, such as computer system 12 (FIG. 1), can be provided and one or more systems for performing the processes of the invention can be obtained (e.g., created, purchased, used, modified, etc.) and deployed to the computer infrastructure. To this extent, the deployment of a system can comprise one or more of: (1) installing program code on a computing device, such as computer system 12 (as shown in FIG. 1), from a computer-readable medium; (2) adding one or more computing devices to the computer infrastructure; and (3) incorporating and/or modifying one or more existing systems of the computer infrastructure to enable the computer infrastructure to perform the processes of the invention.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A system comprising:
a CPU, a computer readable memory and a computer readable storage medium associated with a computing device;
program instructions to monitor a user's communication feeds;
program instructions to parse the user's communication feeds;
program instructions to determine the user's tasks based on parsing the user's communication feeds;
program instructions to determine the user's context switches based on determining the user's tasks;
program instructions to receive biometrics data associated with the user via an application programming interface (API);
program instructions to determine the user's stress levels at various times based on the biometrics data;
program instructions to store information linking the user's stress level with the user's context switches;
program instructions to output the information linking the user's stress level with the user's context switches; and
program instructions to adjust a user's schedule to minimize the user's context switches which have a highest stress value,
wherein the program instructions are stored on the computer readable storage medium for execution by the CPU via the computer readable memory, and
the information linking the user's stress level with the user's context switches comprises a list of the user's context switches over a predetermined period of time, types of the user's context switches, the user's stress level at each context switch, and an aggregate stress level for the user during the predetermined period of time.

2. The system of claim 1, wherein the user's communication feeds includes:
instant messages;
social media activity;
interactive media feed activity;
e-mail messages; and
calendar entries.

3. The system of claim 1, further comprising program instructions to determine an aggregate stress level based on the information linking the user's stress level with the user's context switches.

4. The system of claim 1, further comprising:
program instructions to determine stress levels for a plurality of users meeting particular criteria based on context switches associated with the plurality of users; and
program instructions to output information regarding the stress levels for the plurality of users meeting the particular criteria.

5. The system of claim 4, wherein the criteria includes:
personality type;
job title;
job department; and
job supervisor.

6. The system of claim 1, wherein the user's communication feeds includes:
instant messages;
network usage activity;
interactive media feed activity;
e-mail messages;
calling activity;
calendar entries; and
location data.

7. The system of claim 1, further comprising program instructions to tag the user's context switches with respective timestamps, wherein the program instructions to store the information linking the user's stress level with the user's context switches is based on the respective timestamps.

8. The system of claim 1, wherein the user's context switches comprise a transition from one task to another task.

9. The system of claim 1, wherein the biometrics data includes heart rate variability (HRV), pulse, and muscle tension.

10. The system of claim 1, wherein the biometrics data is captured by a biometric device with at least one biometrics sensor.

11. The system of claim 10, wherein the at least one biometrics sensor comprises a heart rate sensor and a muscle tension sensor.

12. The system of claim 1, wherein the program instructions to parse the user's communication feeds further comprises removing non-pertinent text from the user's communication feeds.

13. The system of claim 1, further comprising program instructions to adjust a plurality of individuals who have a predetermined job title and have the highest stress value.

14. The system of claim 13, wherein the information which is output comprises a stress indicator analysis report which is sorted in descending order of stress indicator values.

15. The system of claim 14, wherein the stress indicator analysis report is based on information stored in a context switching stress table.

16. The system of claim 15, wherein the program instructions to parse the user's communication feeds comprise:
- removing non-pertinent text from text associated with one of the user's communication feeds; and
- extracting subjects and verbs from the user's communication feeds to determine the user's tasks.

17. The system of claim 16, wherein the program instructions to parse the user's communication feeds further comprise:
- determining whether the extracted subjects and verbs from the user's communication feeds match a database which stores pertinent verbs and subjects corresponding to the user's tasks; and
- tagging the extracted subjects and verbs from the user's communication feeds in response to the extracted subjects and verbs from the user's communication feeds matching the database.

* * * * *